United States Patent [19]

Malabarba et al.

[11] Patent Number: 5,438,117
[45] Date of Patent: Aug. 1, 1995

[54] HEXAPEPTIDES DERIVING FROM AGLUCOTEICOPLANIN AND A PROCESS FOR PREPARING THEM

[75] Inventors: Adriano Malabarba, Binasco; Romeo Ciabatti, Novate Milanese, both of Italy

[73] Assignee: Gruppo Lepetit S.p.A., Gerenzano, Italy

[21] Appl. No.: 264,228

[22] Filed: Jun. 23, 1994

Related U.S. Application Data

[63] Continuation of Ser. No. 64,096, May 20, 1993, abandoned.

[30] Foreign Application Priority Data

Dec. 20, 1990 [EP] European Pat. Off. ............ 90124926
Jul. 10, 1991 [EP] European Pat. Off. ............ 91111456

[51] Int. Cl.$^6$ ..................... C07K 9/00; A61K 38/00
[52] U.S. Cl. ................................................. 530/317
[58] Field of Search ............................. 530/317; 514/9

[56] References Cited

PUBLICATIONS

Journal of the American Chemical Society, Perkin Transactions, vol. I, No. 12, 1 Dec. 1989, Letchworth GB pp. 2335-2339.

Primary Examiner—Jill Warden
Assistant Examiner—P. Lynn Touzeau
Attorney, Agent, or Firm—J. Michael Dixon

[57] ABSTRACT

Hexapeptides of formula (I) deriving from aglucoteicoplanin and their salts with acids and bases as well as their inner salts wherein R is hydrogen or a protecting

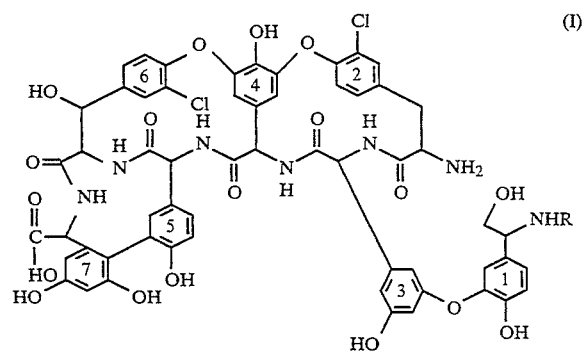

group of the amino function. The products of formula (I), wherein R is hydrogen, possess antimicrobial activity in particular against coagulase-negative strains and some *S. aureus* and *S. epidermidis* strains which have low sensitivity toward teicoplanin. The hexapeptides are produced by reductive cleavage of aglucoteicoplanin with alkali metal borohydrides in the presence of a hydroalcoholic mixture as solvent.

15 Claims, No Drawings

HEXAPEPTIDES DERIVING FROM AGLUCOTEICOPLANIN AND A PROCESS FOR PREPARING THEM

CROSS-REFERENCE TO RELATED APPLICATION

This is a continuation of application Ser. No. 08/064,096, filed May 20, 1993, now abandoned, which is herein incorporated by reference.

This invention concerns an hexapeptide derivative of aglucoteicoplanin which is represented by the following formula (I)

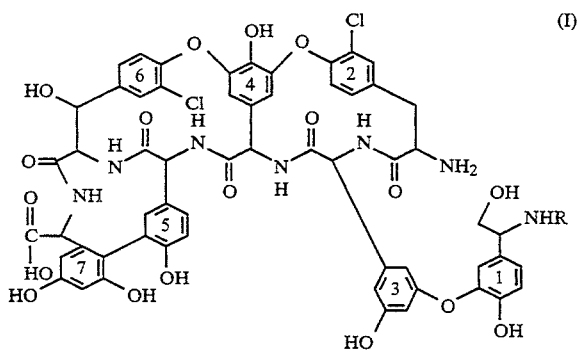

wherein
R is hydrogen or a protecting group of the amino function,
and the salts thereof with acids or bases as well as its inner salts.

The invention includes also a process for producing the hexapeptide of formula (I) from aglucoteicoplanin or a derivative thereof of formula (II)

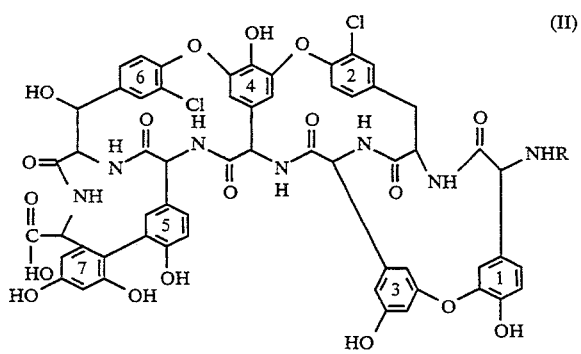

wherein R is hydrogen or a protecting group of the amino function and its salts with acids or bases as well as its inner salts.

Aglucoteicoplanin (formula (II) above, R=hydrogen), i.e. the aglycon of teicoplanin, is a known compound which can be produced by acid hydrolysis of teicoplanin $A_2$ complex (see for instance, European Patent Application Publication No. 376042), an antibiotic which is used for combatting infections from Gram-positive microorganisms.

Some aglucoteicoplanin derivatives protected at the amino function are also known compounds which have been utilized for the preparation of semi-synthetic teicoplanins, e.g. the teicoplanin amides disclosed in European Patent Application Publication No.218099.

The protecting groups which are most frequently employed in the teicoplanin chemistry for protecting the $N^{15}$ amino function are the lower alkoxycarbonyl, e.g. tert-butoxycarbonyl, and the phenyl lower alkoxycarbonyl groups, e.g. benzyloxycarbonyl.

However, any typical protecting group of the amino function which is resistant to the conditions applied during the process of this invention and may be readily removed, can be utilized here.

Suitable protecting groups of the amino function are, for instance, described in: T. W. Greene, "Protective Groups in Organic Synthesis", J. Wiley, New York, 1981.

In particular, in this case, those protecting groups which are formed by acylating the amino function are preferred. Usually, the acylating agents are those reactants providing an alkanoyl or aroyl group, or a carbonate function such as the lower aliphatic acids halides, anhydrides, or activated esters of lower aliphatic acids wherein the aliphatic chain may optionally be substituted by halo or lower alkoxy e.g. acetic, chloroacetic, dichloroacetic, trifluoroacetic, and methoxyacetic acid, the halides, anhydrides or activated esters of aromatic acids wherein the aryl portion may be optionally substituted by halo, lower alkyl, lower alkoxy or nitro, e.g. benzoic, 4-chlorobenzoic, 4-methoxybenzoic, and 2-nitrobenzoic acid, or carbonic acid halides, anhydrides or activated esters, e.g. diethyl carbonate, di-tert-butyl-carbonate, di-tert-butyl-dicarbonate, 2,2,2-trichloro-ethyl chloroformate, allyl chloroformate, benzyl chloroformate, and 2,4,5-trichlorophenyl-tert-butyl-carbonate. The most preferred protecting group of the $N^{15}$ function is tert-butyloxycarbonyl (t-BOC).

The hexapeptides of formula (I) are useful as antimicrobial agents and as intermediates or starting materials, for the production of new synthetic derivatives of aglucoteicoplanin, for instance, aglucoteicoplanin-like products wherein the aryl function of the third aminoacid is modified and a new first aminoacid function is appropriately selected and bound to the N-terminal aminoacid (residue 2 in formula I) of the hexapeptide chain through peptide chemistry reactions.

The process for the production of the hexapeptide of formula (I) from aglucoteicoplanin and its derivatives of formula (II) consists in the reductive hydrolysis of the amide bond linking the first and second aminoacid fragments. This reaction, under the conditions so far utilized, occurs concomitantly with the reductive cleavage of the amide bond linking the second and third aminoacids which yields a pentapeptide of formula (III) wherein R has the same meanings as above. Methods and procedures specifically adjusted to yield this latter compounds are described and claimed in the co-pending European Patent Application Publication No. 409045 and U.S. patent application Ser. No. 07/552,275, now abandoned.

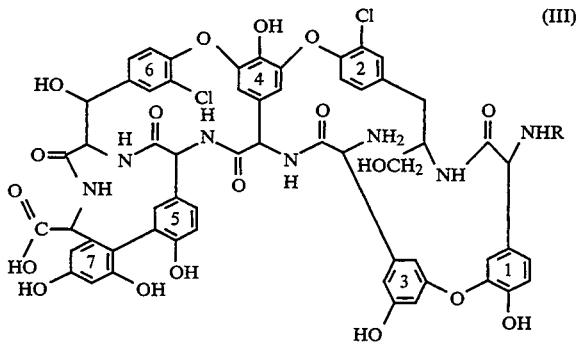

The reaction conditions which allow obtainment of the hexapeptide (I) in the most favorable ratio in the reaction end-product comprise contacting the aglucoteicoplanin derivative of formula (II) with a large molar excess (e.g. from 100 to 300 molar proportions) of an alkali metal borohydride, preferably, sodium borohydride or potassium borohydride in a mixture alkanol:water, at a temperature between 0° and 40° C., preferably, between 10° and 25° C., for period of time sufficient to produce a recoverable amount of hexapeptide of formula (I).

With the term "alkanol" is intended a lower linear or branched $C_1$-$C_4$ alkyl alcohol.

Preferred alkanols are ethanol and iso-propanol with the ethanol being the most preferred one.

With the term "recoverable amount" is intended a certain quantity of product which can be isolated from the reaction mixture by using the common recovery, separation and purification methods, and which is sufficient for the experimental testing and uses disclosed in this specification.

Usually, the reaction time ranges between 10 and 30 hours. The preferred reaction time within this interval depends on the amount of solvent and reducing agent in comparison with that of the substrate, on the temperature and on the type of reducing agent employed and it may be appropriately determined by following the reaction by analytical methods, e.g. by HPLC. In fact, it has been observed that, besides the side-product of formula (III), a further side-product forms under the general conditions of the process of this invention. Such by-product corresponds to the epimer of the hexapeptide of formula (I) at the carbon atom corresponding to the carbon attached to the aryl function identified with the number 3 in the above formula (I), i.e. the aliphatic carbon atom of the third aminoacid fragment of the original aglucoteicoplanin precursor of formula (II).

While the pentapeptide product (III) is a useful product, as shown in the above mentioned co-pending applications, the epimer has no practical utility since it is biologically inactive. Therefore, one of the principal aims of the analytical control of the reaction course is that of having minimized the amount of the epimer in the product resulting from the invention process.

In order to achieve better yields, particular attention has to be made to the mixture alkanol:water. In fact, even if it is possible to prepare the hexapeptide compounds of the invention by starting from a non-protected compound of formula II by employing a mixture ethanol:water in a ratio 4:6 (v/v), preliminary experiments carried out with $N^{15}$ protected compounds of formula II indicated that no significant transformation occurs by employing a mixture ethanol:water in a ratio 2:8 (v/v).

By increasing the ratio alkanol:water, the yields of the product increase and the formation of epimers is substantially decreased. The preferred ratio alkanol:water is comprised between 4:6 (v/v) and 9:1 (v/v).

The best results have been achieved starting from $N^5$ tert-butyloxycarbonyl aglucoteicoplanin and using a solvent mixture ethanol:water 9:1.

Under these conditions, the corresponding protected hexapeptide compound resulted to be the main product with 80% yield. After de-protection with trifluoroacetic acid and purification by column chromatography the desired compound was obtained with an overall yield of about 50%.

Using isopropyl alcohol, instead of ethanol a similar behaviour was observed but relatively longer (30%) reaction times.

Water is essential for the reaction since no transformation occurs in absolute ethanol or isopropanol, thus proving that the mechanism implies an hydrolytical step.

According to the process conditions outlined above, when the reaction is stopped, the excess of the alkali metal borohydride is decomposed by adding a suitable amount of an acid, for example, a ($C_1$-$C_4$) aliphatic acid, a ($C_1$-$C_6$)alkane sulfonic acid, an aryl sulfonic acid, e.g. benzenesulfonic or naphthalenesulfonic acid.

Most of the epimeric inactive product can be eliminated from the reaction mixture by addition of a solvent wherein its solubility is lower than that of the desired product of formula (I), for instance, a solvent selected from lower alkanols or a mixture thereof (e.g. a mixture of methanol and ethanol). The solid which separates, usually as a suspension, is eliminated by filtration or, preferably, by centrifugation.

The resulting solution is concentrated and the insoluble material which forms during this step (mainly boron salts) is filtered off. The remaining solution is chromatographed on silanized silica-gel by eluting first with water and then with a mixture water:acetonitrile 1:1. Fractions are collected and checked by HPLC. The fractions containing the pentapeptide of formula (III) are separated and, if desired, evaporated to recover the relative product. The fractions containing the aglucoteicoplanin hexapeptide of formula (I) are pooled and, then, concentrated and added with a non solvent, such as, diethyl ether to precipitate the crude product of formula (I).

This product may still contain a certain amount of undesired inactive epimer and, therefore, may require a further purification by means of common procedures such as crystallization or column chromatography.

According to a preferred purification method the above mentioned crude product is dissolved in a sufficient amount of water and, then, chromatographed on a silanized silica-gel column by developing with a linear step-gradient of acetonitrile in water and collecting several fractions under HPLC control. The fractions containing pure compound (I) are pooled and evaporated to yield the desired product.

The hexapeptide which is isolated as non-salt form according to the procedure described above, can be transformed into its corresponding addition salts with acids or bases. Representative acid addition salts are those formed by of the amine rests of the hexapeptide with both inorganic and organic acids, for example, hydrochloric, sulfuric, phosphoric, succinic, citric, lactic, maleic, fumaric, cholic, d-glutamic, d-camphoric, glutaric, phthalic, tartaric, methanesulfonic, benzenesulfonic, benzoic, salicylic, trifluoroacetic acid and the like.

The salts with bases are those salts formed by reaction of the carboxylic acid rest of the hexapeptide with a base such as, for instance, an alkali metal hydroxide or carbonate or an organic amine, such as mono-, di- or trialkyl-amines and the like.

The addition salts with pharmaceutically acceptable acids and bases are particularly preferred.

The procedures for transforming the non-salt form into the corresponding salts are those usually employed in the practice and include, for instance, dissolving the non-salt form into an aqueous solvent and adding thereto a slight molar excess of the selected acid or base and then adding a water miscible organic solvent wherein the salt is insoluble, or concentrating the aqueous solution to obtain a precipitate. Analogously, from a salt, the non-salt form can be obtained through reverse operations which includes, for instance, dissolving the salt into an aqueous solvent and adding an acid or base to set free the hexapeptide which can be recovered, for instance, by extraction with a water partially miscible organic solvent.

These procedures can be utilized also for further purification of the hexapeptide derivative.

The "inner salts" are those salts formed by internal salification between acid and base functions contained in the molecule of the hexapeptide (I) and are equivalent to the non-salt form for the description and the uses of the compounds of this invention.

The antimicrobial activity, expressed as minimal inhibitory concentration (MIC), of the hexapeptide of formula (I), R=hydrogen, against selected strains of Gram-positive bacteria was determined in comparison with teicoplanin. The microdilution method in DIFCO TODDO-HEWITT broth (Streptococci) or OXOID ISO-SENSITEST broth (Staphylococci) was used. Final inoculum was about $10^5$ cfu/ml, and MIC was read as the lowest concentration (mcg/ml) which showed no visible growth after 18-24 hours incubation at 37° C.

As reported in Table I below, the above mentioned hexapeptide is generally less active than teicoplanin against Staphylococci and Streptococci, while maintaining the same degree of activity against S. epidermidis and S. haemolyticus, two species of Coagulase-Negative Staphylococci (CNS), but it is four to sixteen times more active against two strains of S. aureus and S. epidermidis low sensitive to teicoplanin.

TABLE I

| | In vitro (MIC, mcg/ml) Activity* | |
|---|---|---|
| ORGANISM Strain | HEXAPEPTIDE (Example 1) | TEICOPLANIN |
| Staph. aureus Tour | 2 | 0.5 |
| Staph. aureus (TLS) | 2 | 8 |
| Staph. epidermidis ATCC 12228 | 0.5 | 0.5 |
| Staph. epidermidis (TLS) | 1 | 16 |
| Staph. haemolyticus clin. isolate (TLS) | 16 | 16 |
| Strep. pyogenes C 203 | 8 | 0.063 |
| Strep. pneumoniae UC 41 | 4 | 0.063 |
| Entero. faecalis | 8 | 0.125 |

TABLE I-continued

| | In vitro (MIC, mcg/ml) Activity* | |
|---|---|---|
| ORGANISM Strain | HEXAPEPTIDE (Example 1) | TEICOPLANIN |
| ATCC 7080 | | |

TLS = Low Sensitive to Teicoplanin
*Inoculum: $10^5$ cfu/ml.

The antimicrobial activity of the hexapeptide derivative of this invention is surprising also in view of the fact that the structural modification in the binding region of the teicoplanin basic structure would have justified a loss of antibacterial activity. In fact, it is known that the binding site responsible of the complexaction of the D-alanyl-D-alanine termins of intermediates of the cell wall biosynthesis, which is the determinant of the common mechanism of action of the antibiotics recently defined as the dalbaheptide group (see: F. Parenti and B. Cavalleri "Novel Glycopeptide Antibiotics of the Dalbaheptide Group", Drugs Of The Future, Vol. 15 (1): 57-72 (1990)), mainly resides in the right hand part of the molecule, as it is shown, for instance, for vancomycin in the paper by N. Pant et al, J. Am. Chem. Soc. 1988; 110: 2002-2003.

The microbiological activity of the hexapeptide deriving from aglucoteicoplanin is even more surprising if it is compared with the biological inactivity shown by the corresponding vancomycin hexapeptide and the corresponding aglycono (See: N. Pant et al, cited above and P. M. Booth et al,: Preparation and Conformational Analysis of Vancomycin Hexapeptide and Aglucovancomycin Hexapeptide J. Chem. Soc. Perkin Trans. I, 1989, 2335-2339).

In view of the above reported antimicrobial activity, the compounds of the present invention can effectively be employed as the active ingredients of the antimicrobial preparations used in human and veterinary medicine for the prevention and treatment of infectious diseases caused by pathogenic bacteria which are susceptible to said active ingredients, in particular, for the treatment of infections caused by Coagulase-Negative Staphylococci and S. aureus and S. epidermidis strains which show low sensitivity to teicoplanin.

The compounds of the present invention can be administered orally, topically or parenterally wherein however, the parenteral administration is preferred.

Depending on the route of administration, these compounds can be formulated into various dosage forms. Preparations for oral administration may be in the form of capsules, tablets, liquid solutions or suspensions. As known in the art, the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations, generally in the form of aqueous or oily solutions or suspensions, may contain conventional additives such as suspending agents.

For topical use the compounds of the present invention may also be prepared in suitable forms for absorption through the mucous membranes of the nose and throat or bronchial tissues and may conveniently take the form of liquid sprays or inhalants, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 1 and about 40 mg of active ingredient per Kg of body weight, preferably divided in 2 to 4 administrations per day. Particularly desirable compositions are those prepared in the form of dosage units containing from about 30 to about 500 mg per unit.

EXAMPLES

The analytical methods and procedures utilized for the characterization of the compounds prepared according to the following examples are described in the separate paragraph following the examples section.

Example 1

Preparation of the aglucoteicoplanin hexapeptide (formula (I), R=hydrogen) by starting from non-protected aglucoteicoplanin To a stirred solution of 100 g (about 80 mmol) of aglucoteicoplanin (formula (II), R=hydrogen) in 3.5 liter of a mixture water:ethanol 6:4 (v/v), 600 g (about 16 mol) NaBH$_4$ pellets is added portionwise in 2 hours, while cooling at 15°-25° C. The reaction mixture is stirred at room temperature for 22 hours, and then it is poured into a solution of 960 ml of glacial acetic acid in 5.5 liter of a mixture methanol:ethanol 65:35 (v/v), while cooling at 10° C. The resulting suspension is centrifuged and the insoluble matter (mainly, inactive epimer) is discarded. The clear solution is concentrated at 45° C., under reduced pressure, to a final volume of about 500 ml, in the presence of n-butanol to avoid foaming.

The resulting suspension is filtered (the insoluble matter, mainly boron salts, is discarded) and then it is loaded on a column of 2.5 Kg of silanized silica-gel (0.06–0.2 mm; Merck) in water. The column is eluted with 10 liter of water and, then, with 10 liter of a mixture acetonitrile:water 1:1 (v/v), while collecting 500 ml-fractions which are checked by HPLC. Fractions 9–16 contain about 105 g of crude pentapeptide of formula III (R=hydrogen). Those fractions (21–30) containing the title compound are pooled and 9 liter of n-butanol are added. The resulting mixture is concentrated at 40° C. under reduced pressure to a small volume (about 200 ml).

After addition of diethyl ether (500 ml), the precipitated solid is collected by filtration and washed with 100 ml of diethyl ether, yielding 49 g of a crude powder containing crude (55%, HPLC titre) title compound and a minor amount of its inactive epimer. The above crude product is dissolved in 500 ml of water and the resulting cloudy solution is loaded on a column of 1.2 Kg of silanized silica-gel in water. The column is developed with a linear step-gradient from 20% to 50% of acetonitrile in water in 20 hours at the flow-rate of 250 ml/hour, collecting 25 ml-fractions. Those fractions containing the pure (HPLC) title compound are pooled and worked up as described above, yielding 18 g of the compound of the title.

Example 2

Preparation of the aglucoteicoplanin hexapeptide (formula (I), R=hydrogen) by starting from a $N^{15}$ protected aglucoteicoplanin 2.1 Preparation of $N^{15}$-tert-butyloxycarbonyl aglucoteicoplanin A solution of 5 g (about 4 mmol) of aglucoteicoplanin, 2 ml of triethylamine (TEA) and 2 g of tert-butyl-2,4,5-trichlorophenylcarbonate in 100 ml of dimethylformamide (DMF) is stirred 24 hours at room temperature. By adding 900 ml of ethyl ether a solid separates which is collected and re-dissolved in 1 liter of a mixture water:methanol 7:3 (v/v). The resulting solution is brought to pH 3.5 with 1N hydrochloric acid, then extracted with 500 ml of ethyl ether, which is discarded. The aqueous layer is extracted again with one liter of n-butanol, and the organic phase is washed with water (2×500 ml), then it is concentrated under reduced pressure at 35° C. to a small volume (about 50 ml). By adding ethyl ether (450 ml) a solid is precipitated which is collected, washed with ethyl ether (2×200 ml) and dried in vacuo at 40° C. overnight, yielding 4.85 g of the title compound.

2.2 Preparation of $N^{15}$-tert-butyloxycarbonyl aglucoteicoplanin hexapeptide

To a stirred solution of 10.5 g (about 8 mmol) of $N^{15}$-tert-butyloxycarbonyl aglucoteicoplanin in 300 ml of a mixture EtOH—H$_2$O 9/1 60 g of NaBH$_4$ (powder) was added portionwise in 2 h (at 20° C.).

Afterwards, stirring was continued at room temperature for 96 h, and then the reaction mixture was slowly poured into 300 ml of a solution MeOH—EtOH—AcOH 3/2/1. After adding 1-BuOH to avoid foaming, the solvents were evaporated at 45° C. under reduced pressure. The solid residue was collected and chromatographed yielding 5.6 g of pure title product.

2.3 Preparation of the aglucoteicoplanin hexapeptide

A solution of 1.1 g of $N^{15}$-tert-butyloxycarbonyl hexapeptide aglucoteicoplanin in 10 ml of dry trifluoroacetic acid (TFA) was stirred at room temperature for 5 min. Afterwards, the solvent was evaporated and the oily residue was slurried with 50 ml of Et$_2$O, yielding 1 g of pure title compound, as the di-trifluoroacetate.

A substantially similar result (50% overall yield from $N^{15}$-tert-butyloxycarbonyl aglucoteicoplanin) was obtained by treating crude $N^{15}$-tert-butyloxycarbonyl hexapeptide aglucoteicoplanin with TFA, followed by a final purification of resulting crude hexapeptide aglucoteicoplanin di-trifluoroacetate by reversed-phase column chromatography. In this case, the aqueous solution of the product to be purified was adjusted at pH 6.5 before loading on the column, thus obtaining pure hexapeptide aglucoteicoplanin as the free base (internal salt).

ANALYTICAL PROCEDURES

1) HPLC method

HPLC analyses were performed on a column Hibar (250×4 mm; Merck) prepacked with Li-Chrosorb RP-8 (10 μm), using a Varian Model 5500 LC pump equipped with a 20 μl-loop injector Rheodyne Model 7125 and a UV variable detector. Chromatograms were recorded at 254 nm. Elutions were carried out at a flow-rate of 2 ml/minute by mixing Eluent A, 0.2% aqueous ammonium formate, with Eluent B, acetonitrile, according to a linear step-gradient programmed as follows:

| Time (minutes): | 0 | 10 | 20 | 30 | 35 | 45 |
|---|---|---|---|---|---|---|
| % of B in A: | 5 | 23 | 26 | 35 | 75 | 5 |

Under these condition the hexapeptide of Example 1, i.e. formula (I) (R=hydrogen), shows a retention time ($t_R$) of 12.6 minutes. Its inactive epimer shows a $t_R$ value of 12.9 minutes.

The $t_R$ value of aglucoteicoplanin is 12.6, i.e. the same as that of the hexapeptide derivative but this fact does not raise major problems since the HPLC analysis is mainly performed on crude reaction product from which the starting aglucoteicoplanin has been almost completely eliminated.

2) Acid base titrations

Acid-base titrations are carried out under the following conditions: the sample is dissolved in a mixture methyl cellosolve:water 4:1, then, an excess of 0.01M HCl in the same solvent mixture is added and the resulting solution is titrated with 0.01N NaOH.

Table 2 shows the equivalent weight of the compound of Example 1.

3) $^1$H and $^{13}$C-NMR

The $^1$H NMR spectra are recorded with a 24 mg solution of the proper product in 0.5 ml of DMSO-$d_6$ at 303° K. on a Bruker AM 500 NMR-spectrometer equipped with an Aspect 3000 computer, using (CH$_3$)$_4$Si (δ0.00 ppm) as internal reference. In particular, in Table 3 are reported only the significative δ values concerning the characteristics portions of the compound of Example 1. For $^{13}$C spectra the spectrometer frequency is 125.17 MHz.

4) FAB-MS

FAB-MS positive ion spectra are obtained on a Kratos MS-50 double mass spectrometer of 3000 dalton mass range, using 8 kV accelerating voltage. The instrument is operating under computer control. To obtain high quality data, a DS-90 data system in "raw data" acquisition is used. For FAB, a saddle field atom gun is used with Xe gas ($2 \times 10^{-5}$ torr pressure indicated on the source ion gauge) at 6 kV voltage and 1 mA current. The samples are dissolved in a mixture methanol:water 1:1 containing 0.2N HCl or, alternatively, in dimethylformamide (DMF). Then, 1 microliter of this solution is mixed with 1 microliter of thioglycerol matrix eventually containing a 1N acetic acid on the target.

Table 2 shows the molecular weight of the compound of Example 1.

TABLE 2

| | Equivalent weight, molecular weight and elemental analysis | | | | | |
|---|---|---|---|---|---|---|
| COM-POUND | Acid-Base Titration (E.W.) | FAB-Mass (M + H)$^+$ | Elemental Analysis[1] Found % | | | |
| | | | C | H | N | Cl |
| Example 1 | 419 (× 3) | 1202 | 57.73 | 4.27 | 7.95 | 5.71 |

[1]Theoretical formula: $C_{58}H_{49}N_7Cl_2O_{18}$; M.W., 1203.0.
Calculated (%): C, 57.90; H, 4.10; N, 8.15; Cl, 5.89.
Elemental analysis is carried out on samples previously dried at 140° C. in $N_2$ atmosphere.

TABLE 3

| $^1$H and $^{13}$C-NMR data in DMSO-$d_6$; (CH$_3$)$_4$Si internal standard, δ 0.00 ppm | |
|---|---|
| COMPOUND Example | δ ppm |
| 1 | $^1$H: 3.58, 3.62 (newly introduced CH$_2$); 4.10–5.96 (peptidic CH's); 6.26–8.52 (aromatic protons and peptidic NH's) |
| | $^{13}$C: 63.76 (CH$_2$OH) |

We claim:

1. A compound of the formula:

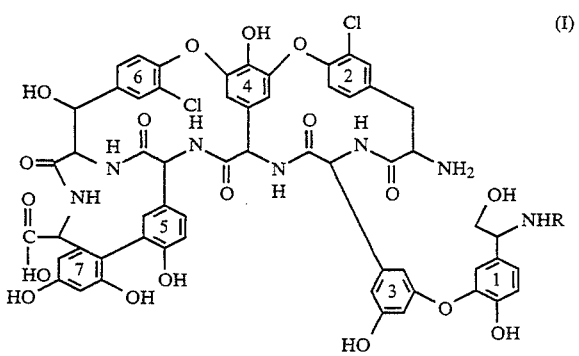

wherein:
R is either hydrogen or a protecting group of the amino function in which said protecting group is a lower alkoxy carbonyl or a phenyl lower alkoxy carbonyl or an acid addition or basic addition salt thereof.

2. A compound of claim 1 wherein R is hydrogen.

3. A process for the manufacture of a compound according to claim 1 which comprises contacting a compound of the formula

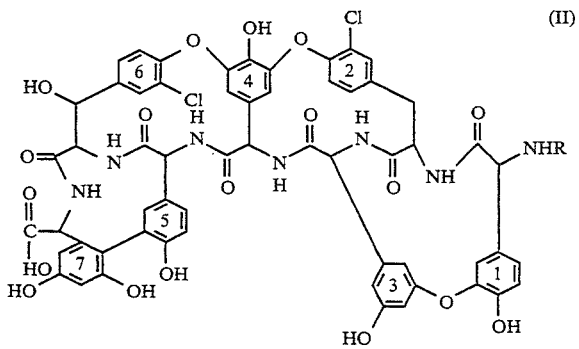

wherein R is defined in claim 1 with a large molar excess of an alkali metal borohydride, in a mixture alkanol:water at a temperature between 0° and 40° C.

4. A process as in claim 3 wherein R is a protecting group of the amino moiety and the mixture ($C_1$–$C_4$) alkyl alcohol:water is at a ratio comprised between 4:6 (v/v) and 9:1 (v/v).

5. A process as in claim 3 wherein R is tert-butyloxycarbonyl and the mixture ($C_1$–$C_4$) alkyl alcohol:water is a mixture ethanol:water in a ratio 9:1 (v/v).

6. A process as in claim 3 wherein the reaction temperature is between 10° and 25° C.

7. A process as in claim 3 wherein the composition is isolated from the other by-products contained in the reaction mixture by addition of a solvent wherein its inactive epimer is less soluble and then chromatographying the filtered solution from which the boron salts have been removed on a silanized silica gel column by eluting first with water and then with a mixture water:acetonitrile whereby the composition is separated from the aglucoteicoplanin pentapeptide side-product.

8. A process as in claim 6 wherein the solvent added for separating the inactive epimer is selected from lower alkanols or a mixture thereof, preferably, a mixture methanol:ethanol.

9. A process as in claim 7 wherein the eluting mixture is water:acetonitrile 1:1.

10. A process as in claim 3 which includes the further step wherein an aqueous solution of the composition is purified by column chromatography on silica gel column by developing with a linear gradient of acetonitrile in water.

11. A process according to claim 3 wherein said alkali metal borohydride is sodium borohydride or potassium borohydride.

12. A pharmaceutical composition comprising an effective amount of a compound according to claim 1 in admixture with a pharmaceutically acceptable carrier.

13. A pharmaceutical composition comprising an effective amount of a compound according to claim 2 in admixture with a pharmaceutically acceptable carrier.

14. A method for the treatment of bacterial infections comprising administering a compound according to claim 1 in an antibacterially effective amount to a patient in need thereof.

15. A method for the treatment of bacterial infections comprising administering a compound according to claim 2 in an antibacterially effective amount to a patient in need thereof.

* * * * *